United States Patent [19]
Garraway et al.

[11] Patent Number: 5,298,145
[45] Date of Patent: Mar. 29, 1994

[54] SIGNAL SUBTRACTION APPARATUS AND METHOD

[75] Inventors: Marcus A. Garraway, Venice; Martin M. Hamano, Torrance; Maynard M. Kepler, Jr., Los Angeles, all of Calif.

[73] Assignee: Hughes Aircraft Company, Los Angeles, Calif.

[21] Appl. No.: 959,577

[22] Filed: Oct. 13, 1992

[51] Int. Cl.⁵ ............................................. G01N 27/26
[52] U.S. Cl. .................................. 204/406; 204/412; 204/434
[58] Field of Search ....................... 204/434, 406, 412; 205/82

[56] References Cited

U.S. PATENT DOCUMENTS

| | | | |
|---|---|---|---|
| 4,132,605 | 1/1979 | Tench et al. | 204/434 |
| 4,631,116 | 12/1986 | Ludwig | 204/434 |
| 4,808,930 | 2/1989 | Kaiser | 204/406 |
| 4,812,210 | 3/1989 | Bonivert et al. | 204/434 |

*Primary Examiner*—John Niebling
*Assistant Examiner*—Bruce F. Bell
*Attorney, Agent, or Firm*—M. E. Lachman; M. W. Sales; W. K. Denson-Low

[57] ABSTRACT

Apparatus and method for stripping off undesirable, high frequency, or alternatively, low frequency components of an input signal by selectively passing only those undesirable components through a filter, and then subtracting those undesirable components from the raw mixture of the desirable and undesirable components. This invention is useful in plating bath analysis.

20 Claims, 3 Drawing Sheets

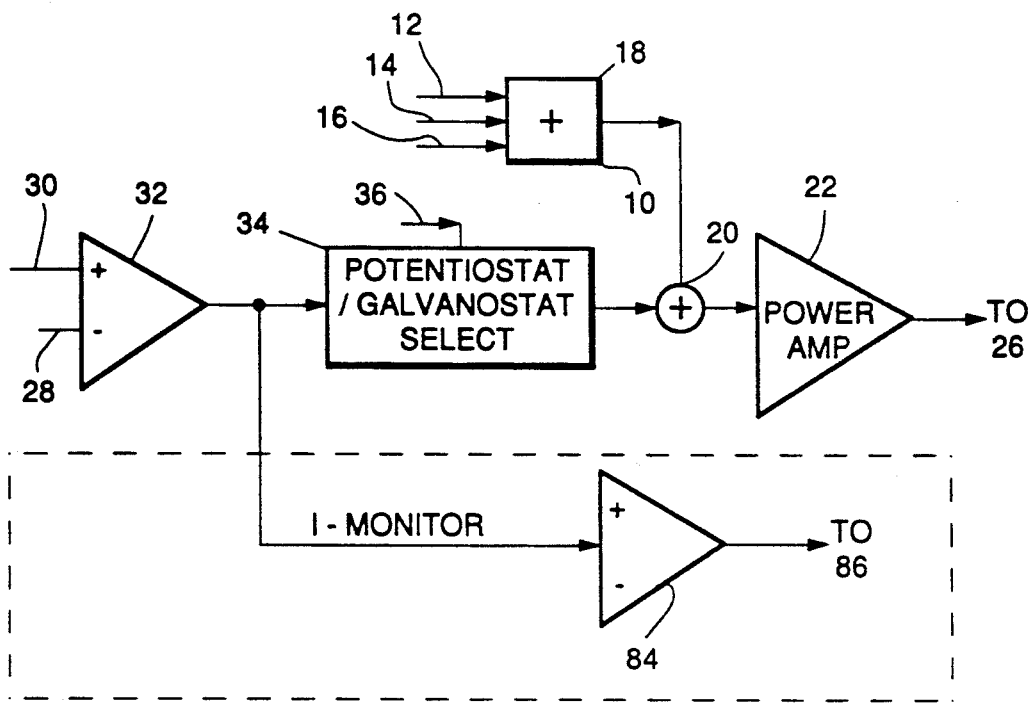
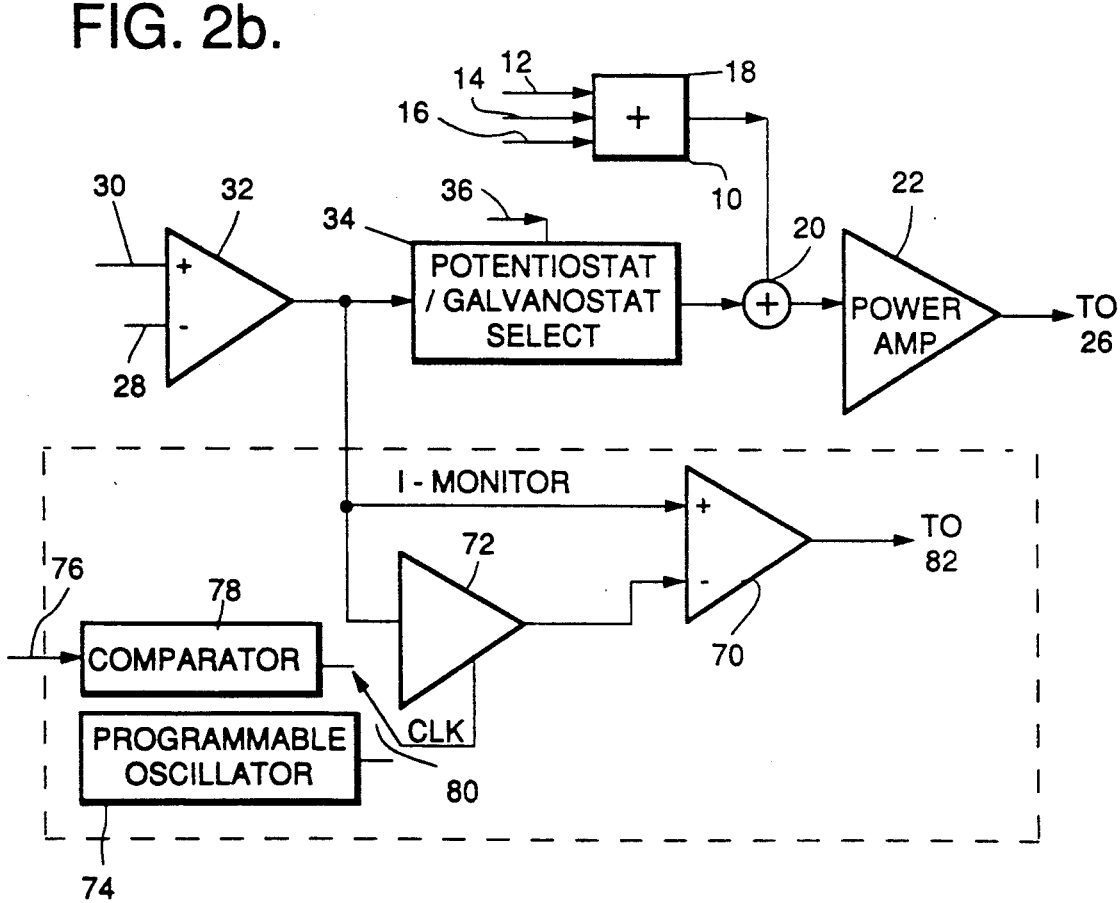
FIG. 2a.
FIG. 2b.

SIGNAL SUBTRACTION APPARATUS AND METHOD

BACKGROUND OF THE INVENTION

1. Field of the Invention

The present invention relates generally to separating low frequency and high frequency components, and more specifically to analysis and feedback from an electrode or probe located in a plating bath.

2. Background of the Invention

Plating is a method of putting an outer coating on the surface of an underlying metal. Popular uses of plating include anodizing the outer surface of aluminum and galvanized steel, and plating copper onto electronic circuit boards. In general, the above plating processes do not require ultra-accurate plating equipment, and can generally accommodate and withstand impurities which may be resident in the plating bath at the beginning of the plating process, or residual impurities, commonly referred to as degradation products.

In many plating applications, however, the characteristics of the plated surface are extremely critical, frequently being more important than the characteristics of the underlying material in some cases. The characteristics of plated coatings usually help determine tensile strength, solderability, brightness, ductility, or flexibility, uniformity of coating, and resistance to thermal or electrical shock. These characteristics of plated coatings are highly dependent on the composition of the plating bath from which they are deposited on an underlying substrate.

Historical platings of copper and the like were made by inserting an electrode made of soft, pure copper into an acid bath, and passing a current through the electrode and the acid bath in order to deposit copper on a circuit board, or the like. The copper that was deposited was usually viewed as a dead, soft grade copper, whose thickness was determined by the current flowing through the electrode, and the amount of time the circuit board spent in the bath. As newer plating surfaces are desired, it has become necessary to apply small amounts of trace elements, compounds, as well as mixtures of plating materials, all in pre-determined quantities, in order to obtain the characteristics of the plating surface required.

This has forced a more analytical evaluation of the composition of the plating bath, both before and during the plating process in order to ensure that the proper mixture of materials is present, and is plated in the desired manner on the base material. U.S. Pat. No. 4,132,605 describes one of the methods which has been used to evaluate the composition of a plating solution. The method involves the application of a DC voltage to a working electrode which is positioned in the plating solution. The voltage is gradually varied in order to pass through both the metal plating voltage range and the metal stripping voltage range. A counter electrode is also placed in the plating solution to aid in the measurements.

This method provides a signal which is related to the plating rate and is useful in evaluating the presence and concentration of elements or compounds that assist or impede the plating process. Unfortunately, not all of the materials which are present in a plating bath will affect the plating rate. Some of the materials will significantly affect the properties of the plated layer, but will not measurably alter the plating or stripping rate. Additional problems are created when a plating bath contains several different elements or compounds which affect the properties of the plated deposit. This is especially difficult when the concentration or presence of one such material affects the way another such material is deposited.

Additional difficulties arise during the aging of the plating solution or plating bath. Aging the plating solution results in the accumulation of trace amounts of impurities and degradation products which interact with each other and material which may be added to the plating bath. It is frequently difficult to determine the precise interactions between the various constituents in the plating bath, and the effect they have on each other, as well as the effect they would have on additional material added to the plating solution.

U.S. Pat. No. 4,631,116, assigned to the present assignee, describes a method for performing a type of spectral analysis on the contents of a plating solution. This method involves applying a gradually varying DC signal to a working electrode located in the plating bath solution. A constant frequency AC signal is superimposed on the DC voltage level. As the DC voltage level is slowly varied, the AC current of the applied AC signal is measured between the working electrode and a counter electrode which is also positioned within the plating solution. The DC voltage level is varied over a pre-determined range which includes voltages which will result in plating and stripping of the plated deposit.

The measurement of the AC current in relation to the varying DC voltage is interpreted as an AC current spectra. The DC voltage level and sweep rate, as well as the AC frequency, are optimized for each of the components within the plating bath in order to properly characterize the contents of the plating bath solution. Analysis of the resulting current spectra is made to develop a fingerprint of the composition of the plating bath. Comparison of the fingerprint of a bath having a known, desirable composition which has resulted in a desirable plating coating with the fingerprint of a plating bath of unknown composition will reveal to an operator the alterations which are required in the unknown plating bath in order to match the composition of the known plating bath, and generate a desired plated surface.

The apparatus used in the application of the method of U S. Pat. No. 4,631,116 includes a reference electrode which is essentially a standard calomel electrode, a working electrode, and a counter-electrode. The counter electrode is the source of the DC voltage and the AC signal superimposed on the DC voltage. The reference electrode or standard calomel electrode provides a reference point from which the voltage applied to the counter electrode is varied.

The method described in U.S. Pat. No. 4,631,116 requires measuring the AC current between the working electrode and a counter electrode and monitoring both the phase angle and quadriture angle of the AC current in order to determine the current spectra. The results of the measurements are recorded on a graphic display and then analyzed or compared with other, known spectra. In employing this method, it is preferable to monitor the second harmonic, which has been found to be more useful than the first harmonic in providing a detailed spectra representative of the contents of the plating bath.

SUMMARY OF THE INVENTION

Accordingly, the need exists for an apparatus which can provide a precise input to the monitoring apparatus, (which includes counter electrode, reference electrode, and working electrode) and can readily and accurately separate the DC component from the AC component of the output of the working electrode in order to provide an accurate measurement of the first and second harmonics of the current measurement.

It is therefore an object of the present invention to provide an apparatus which can readily apply the required signals to the counter electrode, reference electrode, and working electrode.

It is a further object of the present invention to provide an apparatus which can readily separate the DC component from the AC component measured on the working electrode.

It is a further object of the present invention to provide an apparatus which can generally separate the DC component from the AC component of an electronic signal without introducing errors or variations to either the DC signal, or to the AC signal.

It is a further object of the present invention to provide an apparatus which can be readily used with a counter electrode, reference electrode, and working electrode to accurately detect the spectra of a plating solution.

It is a further object of the present invention to provide an apparatus which can readily detect the presence or absence of various components of a plating solution.

The present invention sums the DC and AC input signals supplied by an external DC sweep generator and AC source and applies the combined AC and DC signal to the counter electrode of a probe through an amplifier. The DC component of the signal detected on the reference electrode and working electrode are fed back to the source to modify and monitor the DC component. The apparatus of the present invention detects the AC component of the current monitored by the working electrode and, maintaining the phase integrity of the signal, provides an accurate measure of the first and second harmonics of the AC current component.

BRIEF DESCRIPTION OF THE DRAWINGS

FIGS. 2a and 2b are block diagrams showing alternative preferred embodiments of the voltage supply section of the apparatus in FIG. 1.

DETAILED DESCRIPTION OF A PREFERRED EMBODIMENT

Figure 1:
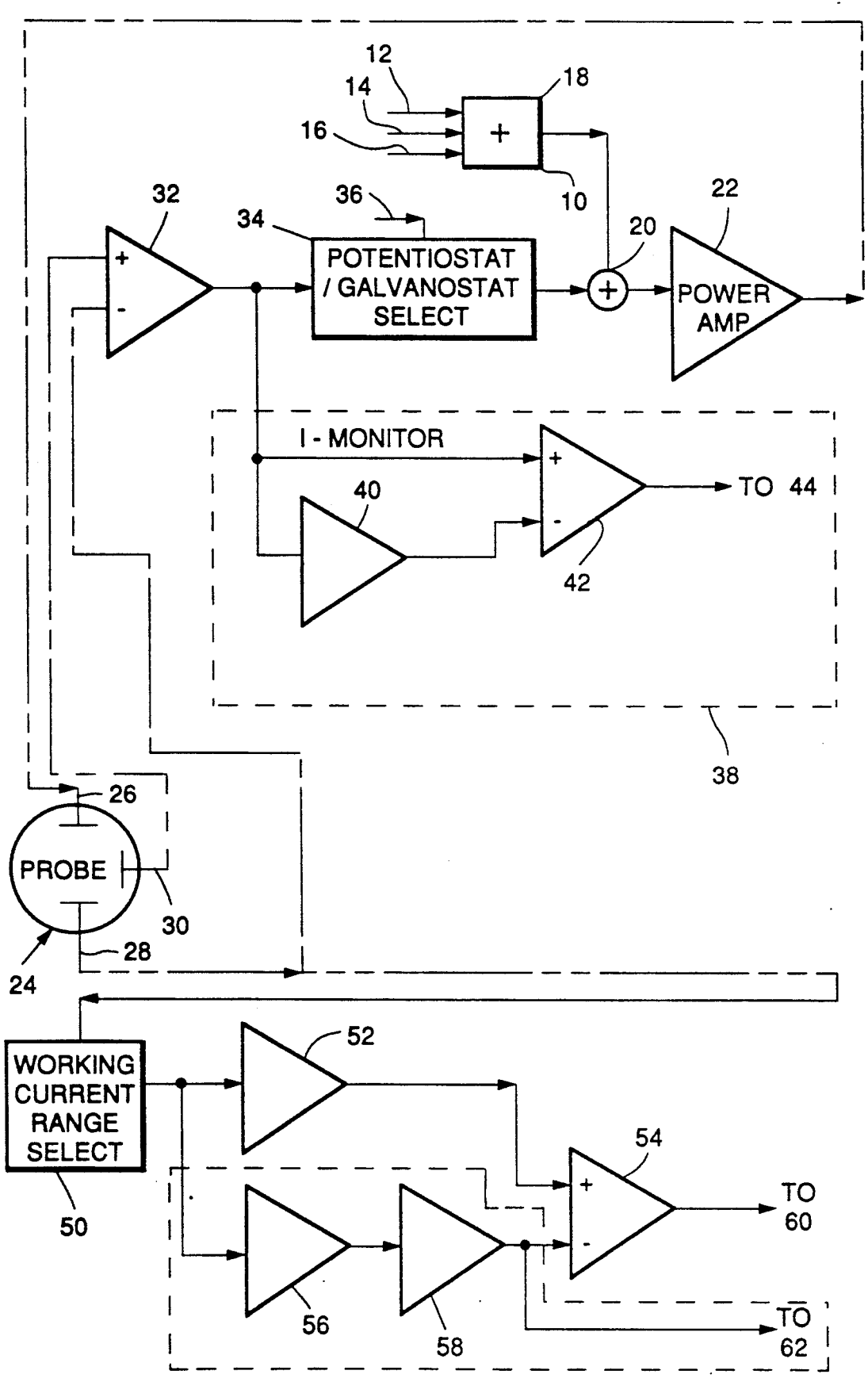
FIG. 1 is a block diagram showing one preferred embodiment of a voltage supply and current detection apparatus in accordance with the present invention.

Referring to FIG. 1, in accordance with the present invention, an alternating current (AC) source 12 which may be a waveform generator is summed with a ramp generator 14 and a direct current (DC) generator 16 by super-positioning the input signals in summer 18. The output of summer 18 is an AC signal which is offset by a gradually increasing DC voltage level.

The AC signal will vary in frequency from at least 10 Hz to 10 kHz to reveal the finest structure of the current spectrum which is possible. The frequency may ultimately be tuned to a single, or series of discrete frequencies in order to optimally detect particular components of the plating bath. The AC voltage level is also varied from at least 5 millivolts to 100 millivolts in order to reveal the finest structure of the current spectrum.

The DC sweep rate is varied from at least 1 millivolt per second to 500 millivolts per second in order to reveal the finest structure of the current spectrum. The DC voltage is varied from approximately 1 volt to approximately −0.2 volts with respect to the standard calomel electrode. These signals are all supplied and controlled by alternating current source 12, direct current generator 16, and ramp generator 14.

The AC frequency and signal strength, as well as the DC sweep rate and DC voltage levels which are produced by embodiments of the present invention are based on the effects of the particular signals and frequencies in revealing the finest structure of the current spectrum possible. The working ranges selected are those specified in U.S. Pat. No. 4,631,116, the contents of which are hereby incorporated by reference. It is recognized that slight or significant deviations from these parameters may be employed in order to reveal a finer spectral structure. It is also recognized that additional signals may be input to summer 18.

As shown in FIGS. 1, 2a and 2b, the output of summer 18 passes through summer 20 and supplies the input to a power amplifier 22. The output of power amplifier 22 drives the counter electrode 26 of probe 24. Summer 20 combines the signal output by summer 18 with a feedback signal generated by reference electrode 30 and working electrode 28.

Probe 24 is submerged in the plating tank. Reference electrode 30 and working electrode 28 provide a differential feedback to electrometer 32. Electrometer 32 behaves substantially as a differential amplifier, outputting a signal which is proportional to the difference between the reference electrode signal and the working electrode signal. The signal output by the electrometer is routed to a potentiostat/galvanostat selection device 34. A measure of the current 36 is also input to potentiostat/galvanostat select 34. The output of potentiostat/galvanostat select 34 is passed through summer 20 to power amplifier 22.

Summer 20 combines the output of the potentiostat/galvanostat select 34 and summer 18, thus adding feedback from reference electrode 30 and working electrode 28 to the AC and DC signals supplied by waveform generator 12, ramp generator 14, and DC generator 16.

The output of electrometer 32 drives a reference voltage generator 38. Reference voltage generator 38 receives a composite signal having AC and DC components from reference electrode 30. The undesired AC component is filtered out of the composite signal and the desired DC component 44 routed to an external data acquisition system. Reference voltage generator 38 may be implemented as a high-pass filter located in parallel with an unfiltered output of the electrometer which drives a differential amplifier 42. The high-pass filter 40 is maintained in its phase relationship with the unfiltered output of the electrometer. The effect of this circuit is to pass the undesirable high frequency components through high-pass filter 40 and to strip out the same undesired high frequency components from the resulting signal by subtracting the output of the high-pass filter from the unfiltered signal which supplies the input to the high-pass filter. This subtraction is done by differential amplifier 42.

The output of differential amplifier 42 thus contains the DC components and the low frequency component signals of the electrometer output. This signal is then supplied to a data acquisition system where it is digitized using a flash converter, or other analog to digital conversion device.

It is critical that no phase shift occur as the signal is passed through the high-pass filter. A phase shift or delay would result in an offset in the form of a phase delay associated with one of the inputs to differential amplifier 42. This would cause an erroneous signal to be generated by the differential amplifier which is not representative of the DC component present in the probe.

Alternatively, the DC component may be ascertained as shown in FIG. 2a, in which a single, low-pass filter 84 is employed to remove the high frequency component of the electrometer output.

Yet another embodiment of a circuit for removing the high frequency component of the electrometer output is shown in FIG. 2b. A high-pass filter 72 drives a differential amplifier 70 in a manner similar to high-pass filter 40 driving differential amplifier 42 as shown in FIG. 1. An additional switching input is provided to the high-pass filter 72. This input controls a universal monolithic switched capacitor filter. Employing a switched capacitor filter allows the pass range of the high-pass filter to be adjusted during operation of the apparatus.

The high-pass filter frequency is adjusted in proportion to waveform 76 which is representative of the signal generated by waveform generator 12. Waveform 76 provides an input to a frequency comparator 78 which provides a clocked output to gradually vary the frequency response of the high-pass filter. This provides a closed loop operation where the frequency cut-off of the high-pass filter can be readily controlled by the same signal which is applied to the counter-electrode 26.

A programmable oscillator 74 can replace waveform input 76 and comparator 78 if desired. The programmable oscillator should be programmed to the same rate at which the waveform generator 12 sweeps through its frequency range. This ensures that the high-pass filter will have the desired frequency pass range. Alternatively, programmable oscillator 74 can be connected to ramp generator 14 if the operator desires to track the pass range of the high-pass filter in proportion to the DC voltage level. A switch 80 allows the operator to switch between comparator 78 and programmable oscillator 74 in controlling the frequency response of the high-pass filter through the switched capacitor filter network.

It is recognized that there are other adaptations of a high-pass filter which can be used to pass the desired high frequency range onto the differential amplifier. Particular implementations include those which track the input frequencies, such as the universal monolithic switched capacitor filter, and others. In addition, it is recognized that a low-pass filter can be employed as shown in FIG. 2a if it does not interfere with the pure DC component of the electrometer signal.

The signal detected by working electrode 28 is a composite signal which includes AC and DC components. The signal detected by working electrode 28 is also routed to a current monitor circuit. As shown in FIG. 1, the signal first passes through a current range select switch 50 and then to two parallel current sense amplifiers 52 and 56. The output of the second current sense amplifier 56 is then routed to a low-pass filter which eliminates high frequency components, and maintains the phase of the output of low-pass filter 58 in phase with the input to low-pass filter 58. This ensures that the output of low-pass filter 58 is in phase with the output of first current sense amplifier 52. The outputs of first current sense amplifier 52 and the output of low-pass filter 58 drive differential amplifier 54.

The low frequency component which is passed through the second current sense amplifier 56 and low-pass filter 58 is used to eliminate the low frequency component of the output signal by canceling the low frequency component which is passed through first current sense amplifier 52. The output of low-pass filter 58 may also be directed to the data acquisition system, as it is representative of the DC component of the current monitoring system formed by the counter-electrode and the working electrode. The output of differential amplifier 54 represents the AC component 60 of the current monitor system and may be routed to a correlation filter located external to the filtering system.

Figure 3:
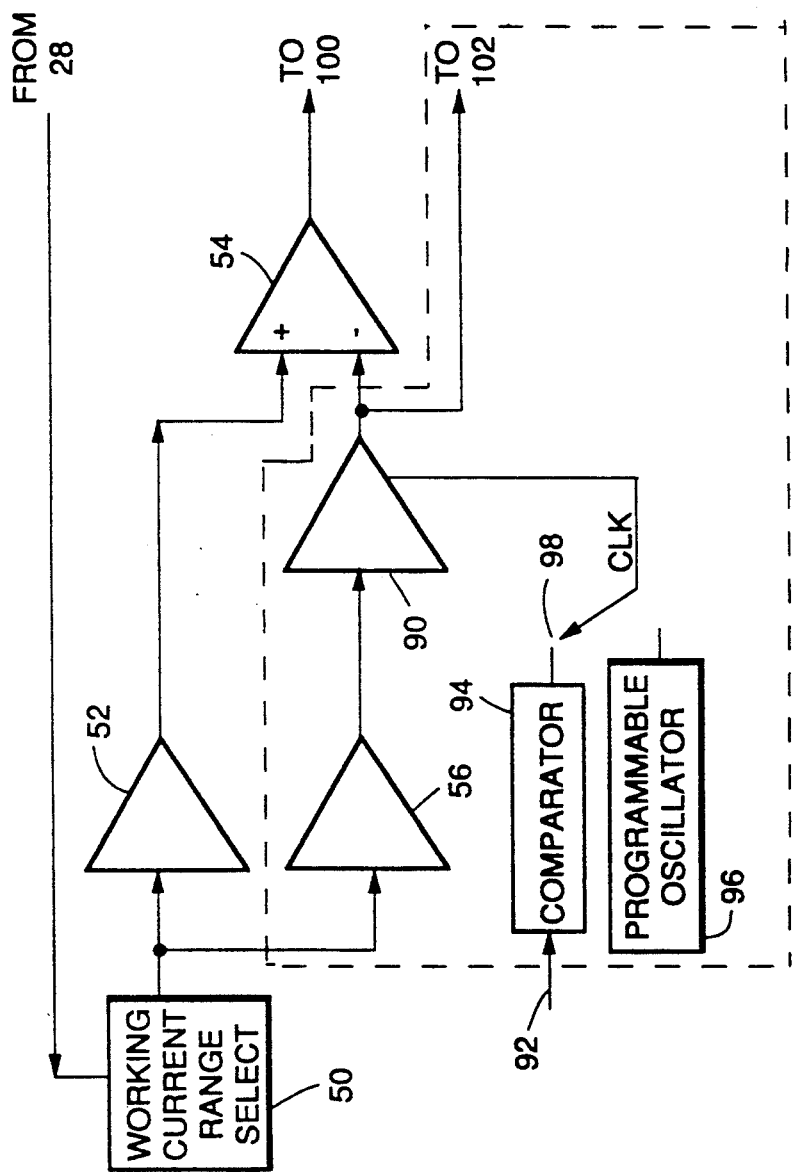
FIG. 3 shows an alternative embodiment of the current detection portion of the apparatus of FIG. 1.

As shown in FIG. 3, the low-pass filter 58 of FIG. 1 can be replaced by a low-pass filter 90 whose frequency pass range is determined by a universal monolithic switched capacitor filter. The switched capacitor filter of low-pass filter 90 is controlled in a similar manner to switched capacitor high-pass filter 72 shown in FIG. 2b. A waveform generator 92 drives a comparator 94 which provides a clock 98 to gradually alter the frequency response of low-pass filter 90 in proportion to the input provided by waveform 92.

Similar to waveform 76, waveform 92 can be derived from waveform generator 12. Alternatively, a programmable oscillator 96 can operate in a manner similar to programmable oscillator 74 of FIG. 2b, and provide a pre-determined, programmable rate of change of the switched capacitor filter of low-pass filter 90. Switch 98 may be manual or electronic, and allows the user or operator to select either a closed-loop mode of operation by driving the low-pass filter 90 with waveform 92, or open loop operation by driving low-pass filter 90 through programmable oscillator 96.

The DC component of the current monitoring system 102 is output by low-pass filter 90 and is routed to a data acquisition system for further processing. Similarly, the AC component of the current monitoring system 100 is output by differential amplifier 54 and is routed to the correlation filter. Output signals 102 and 100 are similar to output signals 62 and 60 of FIG. 1, respectively, but differ because of the selectable pass range of low-pass filter 90 affecting the DC component 102 and the AC component 100 of the current monitoring system.

The apparatus and method of the present invention are particularly useful for providing accurate measurements for plating bath analysis methods previously described. However, it is not intended to limit the present invention to plating bath analysis, but rather to include any system or method in which it is advantageous to separate desirable and undesirable AC signal components from a mixture thereof.

There have been described hereinabove several specific, preferred embodiments of the signal subtractor apparatus and method of the present invention. Those skilled in the art may make numerous uses of and departures from the above-described embodiments without departing from the scope of the present invention which is defined solely by the scope of the following claims.

What is claimed is:

1. An apparatus for monitoring the electrical characteristics of a plating bath comprising:
   a probe having a counter-electrode, a reference electrode, and a working electrode;
   an input signal generator means electrically connected to said counter-electrode which provides a combined DC and AC signal to said counter-electrode wherein said DC signal comprises a voltage and said AC signal comprises an amplitude and frequency;
   a first signal detection means electrically connected to said working electrode which detects a composite; signal comprising a DC signal, AC signal, and current;
   said first signal detection means further monitoring the current detected by said working electrode; and
   said first signal detection means further comprising at least one current filter network having a filter range.

2. The apparatus as described in claim 1 in which said first signal detection means comprises means which detects a composite signal having a DC signal component and an AC signal component, and in which said current filter network further comprises a first filter means which passes the AC signal component and a first differential amplifier means for combines the AC signal component with the composite signal, causing subtraction of the AC signal component from the composite signal.

3. The apparatus of claim 2 in which said first filter means further comprises a controlled filter means having a filter range and pass range which are modified by applying one or more control signals to said controlled filter means.

4. The apparatus of claim 3 in which said input signal generator means further comprises an AC signal generator whose output frequency and voltage are varied by applying one or more control signals to said AC signal generator means.

5. The apparatus of claim 4 in which said controlled filter means comprises means which varies the filter range in proportion to a signal generated by said AC signal generator means.

6. The apparatus of claim 1 and further comprising:
   a second signal detection means for detecting the voltage difference between said reference electrode and said working electrode; and
   a voltage filter network for eliminating AC signals having a frequency range.

7. The apparatus of claim 6 and further comprising:
   a first feedback means having an input which is electrically connected to said reference electrode and said working electrode and an output which is electrically summed with the output of said input signal generator means;
   said summed input generator signal and said first feedback signal supplying the input to said counter-electrode; and
   said first feedback means reducing the amplitude of the signal supplied to said counter-electrode when the signal detected by said working electrode is greater than the signal detected by said reference electrode.

8. The apparatus of claim 6 in which said voltage filter network further comprises:
   a second filter means for passing the AC signal component; and
   a second differential amplifier means for combining the AC component signal which has passed through said second filter means with a mixture of the DC component and AC component signal, causing a subtraction of the AC component signal from the mixture of the DC component and AC component signals.

9. The apparatus of claim 7 in which said second filter means further comprises a controlled filter means whose frequency response and pass range are selectively varied by applying one or more control signals to said controlled filter means.

10. A signal subtraction device comprising:
    at least one input signal generator;
    a probe having at least one input and one output, said inputs connected to said input signal generators, said outputs detecting a composite signal which includes a DC signal component and an AC signal component;
    a signal filter means which passes the AC signal component;
    a differential amplifier means which combines the AC component signal with a mixture of a DC component and AC component signal, causing the subtraction of the AC component signal from the mixture of the DC component and AC component signals; and
    said input signal generator further comprising means which provides a combined DC signal, AC signal, and ramp signal.

11. A signal subtraction device as described in claim 10 in which said signal filter means further comprises a controlled filter means in which the filter range is varied by applying one or more control signals.

12. The device as described in claim 11 in which said controlled filter means further comprises a switched capacitor filter.

13. The device as described in claim 12 in which said switched capacitor filter further comprises a universal monolithic switched capacitor filter.

14. The device as described in claim 10 in which the input signal generator means comprises means which supplies the DC signal and means which applies the AC signal of a frequency and amplitude to said DC signal.

15. The device as described in claim 14 in which said input signal generator comprises a means which controls one or more control signals which determine the DC signal and the AC signal frequency and amplitude.

16. The device as described in claim 10 in which said signal filter means further comprises whose frequency response is controlled by one or more at least one current filter network having a filter range.

17. The device as described in claim 10 in which said signal filter means further comprises at least one voltage filter network having a filter range.

18. The device as described in claim 17 and further comprising:
    a feedback means having an input which is electrically connected to at least one output of said probe;
    said feedback means having an output signal which is electrically summed with the output of said input signal generator means;
    said summed input generator signal and said output of said feedback means signal supplying the input to at least one input of said probe; and
    said feedback means having means which alters the amplitude of the output signal of said feedback means.

19. An apparatus for monitoring the electrical characteristics of a plating bath comprising:
- a probe having a counter-electrode, a reference electrode, and a working electrode;
- an input signal generator means providing a DC bias/offset and an AC signal of an amplitude and frequency;
- said input signal generator means electrically connected to said counter-electrode;
- a first signal detection means electrically connected to said working electrode which detects both the DC signal and AC signal supplied to said probe by said counter-electrode;
- said first signal detection means further monitoring the current detected by said working electrode;
- said first signal detection means further comprising at least one current filter network having a filter range;
- a second signal detection means electronically connected to said working electrode and said reference electrode;
- said second signal detection means which detects the voltage difference between said reference electrode and said working electrode; and
- a voltage filter network eliminates AC signals having a frequency range.

20. The apparatus as described in claim 19 in which said signal detection means comprises means for detecting a composite signal having a DC signal component and an AC signal component, said apparatus further comprising:
- said current filter network further comprising a first filter means which passes the AC signal component and a first differential amplifier means which combines the AC signal component with the composite signal, causing subtraction of the AC signal component from the composite signal; and
- said voltage filter network further comprising a second filter means which passes the AC signal component and a second differential amplifier means which combines the AC component signal which has passed through said second filter means with a mixture of the DC component and AC component signal, causing a subtraction of the AC component signal from the mixture of the DC component and AC component signals.

* * * * *